United States Patent [19]

Muto et al.

[11] Patent Number: 5,284,983
[45] Date of Patent: Feb. 8, 1994

[54] PROCESS FOR PURIFYING AQUEOUS CRUDE ETHANOL SOLUTION

[75] Inventors: Tsunehisa Muto; Futoshi Kanegae, both of Yamaguchi; Toru Takatsuka, Yokohama; Seiya Hirohama, Yokohama; Masazumi Ojiro, Yokohama, all of Japan

[73] Assignee: Basic Industries Bureau of Ministry of International Trade and Industry, Japan

[21] Appl. No.: 965,288

[22] PCT Filed: Mar. 24, 1992

[86] PCT No.: PCT/JP92/00354

§ 371 Date: Feb. 3, 1993

§ 102(e) Date: Feb. 3, 1993

[87] PCT Pub. No.: WO92/21638

PCT Pub. Date: Dec. 10, 1992

[30] Foreign Application Priority Data

Jun. 7, 1991 [JP] Japan .................. 3-162406

[51] Int. Cl.$^5$ ............... C07C 29/86; C07C 29/80; C07C 31/08
[52] U.S. Cl. ............... 568/918; 568/913
[58] Field of Search ............... 568/918, 913

[56] References Cited

U.S. PATENT DOCUMENTS

| | | | |
|---|---|---|---|
| 4,492,808 | 1/1985 | Hagen et al. | 568/913 |
| 4,956,052 | 9/1990 | Hirata et al. | 568/918 |
| 5,185,481 | 2/1993 | Muto et al. | 568/918 |

FOREIGN PATENT DOCUMENTS

| | | | |
|---|---|---|---|
| 129459 | 12/1984 | European Pat. Off. | 568/918 |
| 480040 | 4/1992 | European Pat. Off. | 568/913 |
| 100536 | 5/1986 | Japan | 568/918 |
| 62-25983 | 2/1987 | Japan . | |
| 62-25984 | 2/1987 | Japan . | |
| 62-25985 | 2/1987 | Japan . | |
| 62-29988 | 2/1987 | Japan . | |
| 62-29990 | 2/1987 | Japan . | |
| 49741 | 2/1990 | Japan | 568/918 |
| 27337 | 2/1991 | Japan | 568/918 |

Primary Examiner—Joseph E. Evans
Attorney, Agent, or Firm—Lorusso & Loud

[57] ABSTRACT

Disclosed is a purification process for removing lipophilic impurities contained in an aqueous crude ethanol solution, in particular, for efficiently removing impurities consisting of $C_3$-$C_4$ alcohols. The process involves (a) a first extraction step wherein the aqueous crude ethanol solution is extracted with an extractant for removing the lipophilic impurities, except for the $C_3$-$C_4$ alcohols, contained in the aqueous crude ethanol solution by subjecting the aqueous crude ethanol solution to extraction with the extractant in a pressurized state containing carbon dioxide in a liquidized state or carbon dioxide gas in a supercritical state; (b) a concentration-distillation step wherein a raffinate obtained in the first extraction step is fed to a distilling column to thereby obtain a highly concentrated aqueous ethanol solution from a top of the distilling column and withdraw fraction containing $C_3$-$C_4$ alcohols from the distilling column as a side stream; (c) a second extraction step wherein the side stream is brought into contact with the extract in a pressurized state, obtained in the first extraction step to thereby extract the $C_3$-$C_4$ alcohols contained in the side stream into the extract; and (d) a water washing step wherein the extract in a pressurized state, obtained in the second extraction step, is brought into countercurrent contact with water in a pressurized state under such a condition that a ratio of the weight of water to the weight of the extract is set to 0.3 or less to thereby recover the ethanol contained in the extract into an aqueous phase.

7 Claims, 1 Drawing Sheet

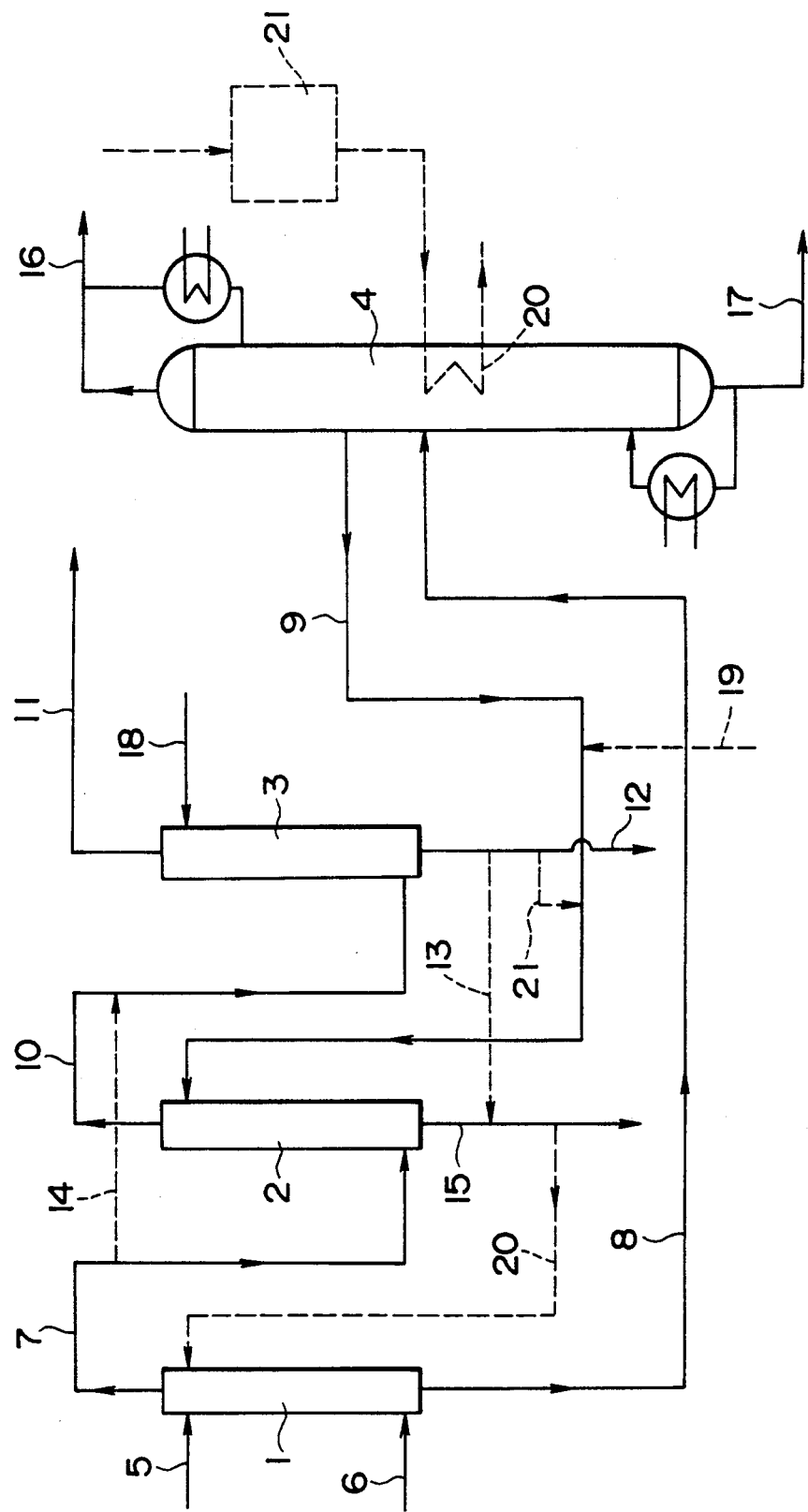
FIG. I

PROCESS FOR PURIFYING AQUEOUS CRUDE ETHANOL SOLUTION

TECHNICAL FIELD

The present invention relates to a process for purifying an aqueous crude ethanol solution.

BACKGROUND ART

Ethanol may be prepared by fermenting sugars such as molasses or by hydrating ethylene (hereinafter referred to sometimes as fermentation method and synthesis method, respectively).

Ethanol preparable by the fermentation method or by the synthesis method is an aqueous crude ethanol solution which is contaminated with various kinds of impurities. Major impurities contained in the aqueous crude ethanol solution prepared by the fermentation method include a variety of compounds, such as methanol, acetaldehyde, n-propanol, n-butanol, ethyl acetate, 3-methylbutanol, and so on. On the other hand, major impurities contained in the aqueous crude ethanol solution prepared by the synthesis method also include a variety of compounds, such as acetaldehyde, diethylether, acetone, sec.-butanol, n-butanol, crotonaldehyde, and so on.

As described hereinabove, the various kinds of impurities are contained in the aqueous crude ethanol solution, yet they are so minute in amount that the removal of such impurities is very difficult. In particular, alcohols having three or four carbon atoms (hereinafter referred to as $C_3$-$C_4$ alcohols) are so similar in their physicochemical properties to ethanol that it is extremely difficult to remove them, as compared with the other impurities.

The distillation has generally been employed to purify an aqueous crude ethanol solution containing the various kinds of the sugars as described hereinabove. This distillation method requires a large number of distilling columns and it consumes a large quantity of steam for distillation. Further, at least one of the plurality of the distilling columns is operated by the extractive distillation method in such a manner that a crude ethanol once concentrated by distillation is added again to a large volume of water and the resulting mixture is fed to the extractive distilling column.

In addition, the $C_3$-$C_4$ alcohols among the impurities can be removed by withdrawing a side stream from the side of the distilling column for concentrating the ethanol; however, a large amount of the ethanol is also withdrawn from the distilling column so that the withdrawn side stream is further distilled in vacuo to thereby recover the ethanol.

Hence, the conventional process for the purification of ethanol using a large number of distilling columns is very poor in efficiency of energy.

In order to improve the problem with the poor efficiency in energy as seen in the distillation method as described hereinabove, a process is proposed in Japanese Patent Laid-open Publication (kokai) Nos. 60-41,627 and 2-49,741, which involves removing lipophilic impurities contained in an aqueous crude ethanol solution by extraction with carbon dioxide in a liquidized state or with carbon dioxide gases in a supercritical state (hereinafter referred sometimes to as carbon dioxide extraction method).

By the term "lipophilic impurities" referred to herein is meant oxygen-containing compounds having two or more carbon atoms, except for ethanol. The aqueous crude ethanol solution preparable by the fermentation method contains methanol as a hydrophilic impurity, in addition to the lipophilic impurities.

The carbon dioxide extraction method can separate the lipophilic impurities as an extract and provide a mixed aqueous solution of a highly purified ethanol and methanol as a raffinate. The rate of extraction (removal) of the lipophilic impurities in this case increases in proportion to an increase in a ratio of an extractant (that is, a ratio of the weight of the extractant to the weight of the aqueous crude ethanol solution), and the predetermined lipophilic impurities can be extracted as the ratio of the extractant reaches to a somewhat large extent. The minimal ratio of the extractant may vary with the concentration of ethanol in the aqueous crude ethanol solution, the composition or the concentration of the impurities, the acceptable range of the impurities in purified ethanol, or the like. Further, the higher the ratio of the extractant, the larger the amount of the extractant to be employed; hence, a high pressure extraction column and a compressor should be made so large in scale and size that costs of equipment become expensive and costs of power required for the compression and the circulation of carbon dioxide gases become high.

It can be noted herein that the $C_3$-$C_4$ alcohols are the lipophilic impurities contained in the aqueous crude ethanol solution, that are the most difficult to extract upon the extraction with carbon dioxide in the liquidized state or carbon dioxide gases in the supercritical state. In the conventional processes, a considerably large amount of the $C_3$-$C_4$ alcohols are left unremoved in the raffinate although almost all amounts of the other lipophilic impurities can be extracted at a certain ratio of the extractant; hence, the ratio of the extractant should be increased to a higher extent in order to extract all the amounts of the lipophilic impurities.

The present invention has the object to provide a process for the purification of an aqueous crude ethanol solution, so adapted as to efficiently separate and remove $C_3$-$C_4$ alcohols from the aqueous crude ethanol solution without causing any increase in the ratio of the extractant.

DISCLOSURE OF INVENTION

More specifically, the present invention is to provide a process for the purification of the aqueous crude ethanol solution, which comprises: (i) a first extraction step wherein the aqueous crude ethanol solution is extracted with an extractant for removing the lipophilic impurities, except for the $C_3$-$C_4$ alcohols, contained in the aqueous crude ethanol solution by subjecting the aqueous crude ethanol solution to extraction with the extractant in a pressurized state, which comprises carbon dioxide in a liquidized state or carbon dioxide gas in a supercritical state; (ii) a concentration-distillation step wherein a raffinate obtained in the first extraction step is fed to a distilling column to thereby obtain a highly concentrated aqueous ethanol solution from a top of the distilling column and withdraw a fraction containing $C_3$-$C_4$ alcohols from the distilling column as a side stream; (iii) a second extraction step wherein the side stream is brought into contact with the extract in a pressurized state, obtained in the first extraction step, to thereby extract the $C_3$-$C_4$ alcohols contained in the side stream into the extract; and (iv) a water washing step wherein the extract in a pressurized state, obtained in the second extraction step, is brought into countercurrent contact with water in a pressurized state under such a condition that a ratio of the weight of the water to the weight of the extract is set to 0.3 or less to thereby recover the ethanol contained in the extract into an aqueous phase.

The present invention can advantageously be applied to either aqueous crude ethanol solution, whether it is an aqueous ethanol solution prepared by the fermentation method or a roughly distilled aqueous ethanol solution prepared by distilling the aqueous ethanol solution prepared by the fermentation method. The aqueous ethanol solution obtained by the fermentation method may generally contain ethanol at the rate of from 10% to 40% by weight and, when the roughly distilled aqueous crude ethanol solution is employed, it is employed as it is or it is employed in the form of an aqueous solution in which the concentration of the ethanol is diluted to from 10% to 50% by weight.

The extractant to be employed for the present invention may include carbon dioxide in the liquidized state or carbon dioxide gases in the supercritical state. For the process according to the present invention, it is preferred to use the carbon dioxide sustained at pressure in the range of from 40 to 150 kg/cm$^2$ and at temperature in the range of from 20° C. to 50° C.

Now, a description will be made of the ratio of the extractant in the first extraction step with reference to the results shown in Table 1 for working examples as will be described hereinafter. The rate at which the lipophilic impurities contained in the aqueous crude ethanol solution are extracted is increased in accordance with an increase in the ratio of the extractant. For example, the lipophilic impurities, except for propanol and butanol, can be extracted and removed at the rate of 98.5% or higher when the ratio of the extractant is set to 2.0 and at the rate of 99.9% or higher when the ratio of the extractant is set to 4.0. On the other hand, propanol and butanol can be removed at the rate of 79% or lower when the ratio of the extractant is set to 2.0 and, when the ratio of the extractant is to set 4.0, butanol can be removed at the rate of 99% or higher yet propanol can be removed at the rate of approximately 73%. In order to allow propanol to be removed at the rate of 98.5% or higher, however, it is needed to raise the ratio of the extractant to 8 or higher. Hence, it can be understood that the ratio of the extractant at which only the lipophilic impurities except for propanol and butanol can be extracted at the rate of 98.5% is sufficient to be a quarter of the ratio of the extractant of 8, at which all the lipophilic impurities containing propanol and butanol can be removed at the rate of 98.5%.

It can be noted that the first extraction step of the process according to the present invention is operated with the main purpose to remove the lipophilic impurities, except for the $C_3$-$C_4$ alcohols, contained in the aqueous crude ethanol solution, so that the conditions are adopted in the first extraction step so as to comply with a desired rate of removal of the lipophilic impurities except for the $C_3$-$C_4$ alcohols. Generally, the condition is such that the ratio of the extractant is in the range of from 2 to 5, preferably from 3 to 4.5. Accurately, however, the ratio of the extractant should be selected by experimental data because the rate of extraction varies to a subtle extent in accordance with the concentration of ethanol and impurities contained in the aqueous crude ethanol solution, the temperature or pressure of extraction, or the like.

The raffinate obtained in the first extraction step is subjected to distillation after gases were removed. The removal of the gases is carried out by removing the carbon dioxide gases, used as the extractant, by vaporization of the carbon dioxide in the liquidized state. The modes of distillation may vary with the concentration of ethanol of the raffinate, and it is usually carried out at ambient pressure or at reduced pressure of approximately 500 mmHg through a tray type distilling column having a theoretical number of nearly thirty stages. In this mode of distillation, a fraction rich in a $C_3$ alcohol or in the $C_3$-$C_4$ alcohols is withdrawn from a middle stage of the distilling column as a side stream, and a highly concentrated mixture of aqueous solution of highly purified ethanol and methanol is extracted from the top of the distilling column. The material to be withdrawn as the side stream is a mixture of a liquid phase with a gaseous phase. Further, by appropriately selecting the reflux ratio and the amount of the mixture to be withdrawn, the $C_3$-$C_4$ alcohols can be removed to a sufficient extent and the concentration of the $C_3$-$C_4$ alcohols contained in the mixed aqueous solution of ethanol and methanol, obtained from the column top, can be sustained within an acceptable range of concentration.

In the process according to the present invention, in particular, when a crude ethanol having the concentration of ethanol in the range of from 80% to 90% is employed as a raw material, the raffinate containing ethanol at the concentration of 30% to 40% can be obtained from a bottom of the first extracting column, so that the process according to the present invention can present the advantage that the load imposed upon the distilling column is lowered and the distilling column can be made smaller in size. In this case, it can further offer the advantages that energy can be saved by allowing a heat source having a relatively low quality, such as low pressure steam, and a highly efficient heat pump to be employed, because a side reboiler for the distilling column can be heated with a heat source having a relatively low temperature.

In the process according to the present invention, the side stream is fed at elevated pressure to the second extraction step, and it is brought into countercurrent contact with the extract in the pressurized state, obtained in and fed from the first extraction step. In the second extraction step, the $C_3$-$C_4$ alcohols contained in the side stream are separated as the extract and a portion of the ethanol is recovered as a raffinate.

The ratio of the extractant in the second extraction step, i.e. a ratio of the weight of the extract from the first extraction step to the weight of the side stream from the distillation step, can appropriately be determined in accordance with the ratio of the extractant in the first extraction step and the amount of the withdrawn side stream. In other words, a large majority of the carbon dioxide fed in the first extraction step is extracted as the extract in the first extraction step, while the side stream in the distillation step usually amounts for approximately 20% to 30% of the aqueous crude ethanol solution, so that there is employed the ratio of the extractant of from approximately 6.0 to 20.0, which is three to five times the ratio of the extractant for the first extraction step. Hence, the rate of removal of the $C_3$-$C_4$ alcohols may become as high as 90% or higher, as will become apparent from Table 3 for the working examples as will be described hereinafter. To the contrary, however, the quantity of ethanol accompanying the extract increases, thereby resulting in an increase in the quantity of the ethanol which will be lost by following the extract in the final water washing step. Hence, for the process according to the present invention, a portion or an entire portion of the aqueous phase of the water washing step is mixed with the side stream and the mixture is recirculated to the second extraction step or only a portion of the extract from the first extraction step is fed to the second extraction step, while the rest of the extract is adjusted for its ratio of the extractant by feeding it to the water washing step or by any other appropriate procedures. Finally, the extract withdrawn from the second extraction step is fed to the water washing step in such a state that it is pressurized, and it is brought into countercurrent contact with water to thereby recover ethanol. In this stage, a ratio of the weight of the washing water to the weight of the extract may usually be set to 0.3 or lower, preferably to from 0.02 to 0.10.

BRIEF DESCRIPTION OF THE DRAWINGS

FIG. 1 is a flow diagram suitable for carrying out the according to the present invention.

BEST MODE FOR CARRYING OUT THE INVENTION

As shown in FIG. 1, an aqueous crude ethanol solution containing ethanol and impurities is introduced into an upper portion of a first extracting column 1 through a line 5, while an extractant consisting of carbon dioxide gases in a pressurized state is introduced into a lower portion of the first extracting column 1 through a line 6.

In the first extracting column 1, the aqueous crude ethanol solution is allowed to come into countercurrent contact with the extractant.

The ratio of the extractant (the ratio of the weight of the extractant to the weight of the aqueous crude ethanol solution) within the first extracting column 1 is so selected as for the rate of extraction of all the lipophilic impurities, except for the $C_3$–$C_4$ alcohols, to amount to a predetermined rate of removal or higher. The ratio of the extractant is usually set to 2 or higher, preferably from 3 to 4.5.

At the conditions as described hereinabove, the substantially entire quantity of the lipophilic impurities, except for the $C_3$–$C_4$ alcohols, contained in the aqueous crude ethanol solution is allowed to migrate into the extract phase to thereby provide the extract consisting of the lipophilic impurities other than the $C_3$–$C_4$ alcohols, a portion of the $C_3$–$C_4$ alcohols, water, ethanol, and a small quantity of methanol.

The resulting extract is then introduced in a pressurized state into the lower portion of a second extracting column 2 through a line 7. On the other hand, a raffinate phase consisting of water, ethanol, methanol and the remaining unextracted $C_3$–$C_4$ alcohols is remained at the bottom of the first extracting column 1. The raffinate phase is then withdrawn from a line 8 and fed to a concentration-distillation column 4 after the gases were removed.

Then, by appropriately selecting the reflux ratio of the concentration-distillation column 4 and the quantity of the side stream to be withdrawn from the middle stage of the column, a highly concentrated ethanol is withdrawn through a line 16 from a top of the concentration-distillation column 4, the highly concentrated ethanol being substantially free from the lipophilic impurities yet containing a small quantity of methanol. At the same time, a fraction containing the substantially entire quantity of the $C_3$–$C_4$ alcohols remaining in the raffinate phase fed from the line 8 is withdrawn from the middle stage of the concentration-distillation column 4 through a line 9 as a side stream. Further, exhaust liquid is withdrawn through a line 17 from the bottom of the column.

The side stream is fed to the top of the second extracting column 2 through the line 9, and it is allowed to come into countercurrent contact with the extract fed from the first extracting column 1 through the line 7 into the bottom of the second extracting column 2. The ratio of the extractant (the ratio of the weight of the extract fed from the first extracting column 1 to the weight of the side stream) in the countercurrent contact is basically determined by the quantity of the extractant fed into the first extracting column 1 and the quantity of the side stream in the concentration-distillation column 4, and it is in the range of usually from 6 to 20, preferably from 6 to 12. In the range of the ratio of the extractant as described hereinabove, the $C_3$–$C_4$ alcohols within the side stream can be extracted into the extract at the rate of 90% or higher. On the other hand, a considerably large quantity of ethanol contained in the side stream is recovered as a raffinate into which a small amount of the lipophilic impurities is in turn extracted from the extract existing in the line 7.

The extract obtained from the top of the second extracting column 2 is fed to a water washing column 3 while it is in a pressurized state through a line 10. A raffinate is withdrawn from the bottom of the water washing column 3 through a line 15, and preferably at least a portion of the raffinate is recirculated to the top of the first extracting column 1 through a line 20.

In the water washing column 3, the extract fed from the line 10 into the bottom of the water washing column 3 in the pressurized state is allowed to come into countercurrent contact with washing water fed from a line 18. The extract fed from the line 10 into the water washing column 3 contains ethanol extracted in the first and second extracting columns, and the countercurrent contact allows the ethanol existing in the extract to be extracted into the washing water. The weight ratio of water (the ratio of the weight of water to the weight of the extract) in the water washing column 3 is usually set to 0.3 or below, preferably in the range of from 0.02 to 0.1. After washing with water, the extract is withdrawn from the top of the water washing column 3 through a line 11. On the other hand, the washing water is withdrawn from the bottom of the water washing column 3 through a line 12. In the water washing column 3, however, a small quantity of the $C_3$–$C_4$ alcohols as well as ethanol are extracted into the washing water so that, preferably, at least a portion of the washing water is mixed with the side stream of the line 9 while passing through a line 21 and it is then fed to the second extracting column 2.

Bypass lines 13 and 14 may be employed in order to appropriately adjust the ratio of the extractant in the second extracting column 2 and the weight ratio of water in the water washing column 3. Further, water may be introduced from a line 19 into the side stream in order to adjust the concentration of ethanol in the second extracting column 2.

In addition, in the process according to the present invention, the concentration of the aqueous ethanol solution to be fed to the distilling column 4 may reach 30% to 40% by weight, so that a side reboiler 20 may be provided and arranged to be heated with a low quality heat source. As a result, such a low quality heat source and a highly efficient heat pump 21 may be employed.

EXAMPLES

The present invention will be described in more detail by way of examples.

EXAMPLE 1

(a) First extraction step:

A sample solution similar to an aqueous crude ethanol solution obtainable by fermentation method yet containing somewhat more impurities was extracted in the first extraction step in which a column, 38 mm in inner diameter and 3 meters in height, having a ¼ inch Raschig ring filled therein, was employed as a first extracting column. As the sample solution, there was employed a solution in which an aqueous ethanol solution having the concentration of 40% by weight of ethanol was mixed with each of impurities consisting of methanol, isoamyl alcohol, n-propanol, n-butanol, ethyl acetate, and acetaldehyde at the rate of 0.2% by weight.

The sample aqueous solution was fed from the top of the first extracting column at the rate of 500 grams per hour, and an extractant consisting of carbon dioxide gases in a supercritical state was fed from the lower portion of the first extracting column so as to provide a predetermined ratio of the weight of the extractant to the weight of the aqueous solution (G/L). The pressure within the column was set to 100 kg per cm$^2$, and the temperature within the column as a whole was maintained at 40° C.

In order to analyze the ingredients of the extract, the extract was withdrawn from the top of the first extracting column and an aqueous ethanol solution was obtained by treating the extract at reduced pressure and vaporizing the extractant only. On the other hand, a raffinate was withdrawn from the bottom of the first extracting column, and an aqueous ethanol solution was obtained by treating the raffinate at reduced pressure and vaporizing the extractant only.

Table 1 below shows rates (percentage by weight) of extraction of the ingredient of the impurities contained in the extract as obtained in the extraction experiments as described hereinabove.

TABLE 1

| G/L (wt/wt) | 1.0 | 2.0 | 3.0 | 4.0 | 5.0 | 6.0 | 7.0 | 8.0 | 9.0 | 10.0 |
| --- | --- | --- | --- | --- | --- | --- | --- | --- | --- | --- |
| EtCHO | 7.70 | 15.40 | 23.10 | 30.80 | 38.50 | 46.20 | 53.90 | 61.56 | 69.04 | 76.07 |
| MeCHO | 72.87 | 98.65 | 99.77 | 99.91 | 99.95 | 99.97 | 99.97 | 99.98 | 99.98 | 99.99 |
| i-AmOH | 85.04 | 99.44 | 99.88 | 99.95 | 99.97 | 99.98 | 99.98 | 99.98 | 99.99 | 99.99 |
| n-BtOH | 40.42 | 79.27 | 96.46 | 99.15 | 99.68 | 99.84 | 99.90 | 99.93 | 99.95 | 99.96 |
| n-PrOH | 18.40 | 36.80 | 55.19 | 73.05 | 86.98 | 94.32 | 97.39 | 98.67 | 99.24 | 99.52 |
| Et—Ace | 99.94 | 99.98 | 99.99 | 99.99 | 99.99 | 99.99 | 99.99 | 99.99 | 99.99 | 99.99 |
| MeOH | 3.90 | 7.80 | 11.70 | 15.60 | 19.50 | 23.40 | 27.30 | 31.20 | 35.10 | 39.00 |

(b) Distillation & separation of raffinate from first extraction step:

By using a distilling column of a batch type, 3.8 mm in inner diameter and 3 meters in height, having a Dickson packing filled therein, the raffinate obtained at the G/L of approximately 3.0 in the first extraction step was distilled to thereby recover ethanol. The concentration of ethanol in the raffinate in this case was approximately 27% by weight, and the concentration of propanol was 0.1% by weight.

The distillation was carried out at the reflux ratio of approximately 3 in the distilling column and the fractions withdrawn one after another from the top of the column, each amounting to the volume of approximately 300 cm$^2$, were analyzed for their ingredients. The analysis results are shown in Table 2 below. In this distillation treatment, fractions Nos. 1 to 3 were recovered as a purified aqueous ethanol solution, and fraction No. 4 was recovered as a side stream.

It can be noted herein that, as far as this distillation treatment is concerned, an aqueous ethanol solution of an extremely high purity, containing extremely small (undetectable) quantities of propanol and butanol, can be yielded, if only the fractions Nos. 1 and 2 are recovered as a purified aqueous ethanol solution. In this case, the fractions Nos. 3 and 4 are to be recovered as a side stream.

TABLE 2

| Fraction No. | Ethanol | Propanol | Butanol | Methanol | Volume of Fraction (mm$^2$) |
| --- | --- | --- | --- | --- | --- |
| 1 | 90.4 | — | — | 3.8 | 300 |
| 2 | 92.1 | — | — | 2.0 | 300 |
| 3 | 89.6 | 0.005 | — | 0.5 | 300 |
| 4 | 61.0 | 0.9 | 0.042 | 0.2 | 300 |
| 5 | 3.0 | 0.001 | — | — | 300 |
| 6 | 1.0 | — | — | — | 300 |

(c) Second extraction step:

The fraction No. 4 obtained in the separation by distillation as described in paragraph (b) above was employed as a side stream in the second extraction step in which a column, 3.8 mm in inner diameter and 3 meters in height, having Raschig rings filled therein, was employed as a second extracting column. In the second extracting column, the extract obtained in the first extraction step at the G/L ratio of 3.0 was fed at the rate of 1,200 grams per hour into the bottom of the second extracting column. The side stream was fed from the top of the second extracting column so as to provide a predetermined ratio of the extractant (the ratio of the weight of the extract to the weight of the side stream). The pressure within the column was set to 100 kg per cm$^2$ and the temperature within the column as a whole was maintained at 40° C. The extract was withdrawn from the top of the second extracting column, and the lipophilic impurities were recovered by treating the extract at reduced pressure and vaporizing the extractant only. On the other hand, the raffinate was withdrawn from the bottom of the column, and an aqueous ethanol solution was recovered by treating the raffinate at reduced pressure and vaporizing the extractant only. Table 3 below shows rates of extraction of the ingredients of the impurities (% by weight of each of the ingredients) contained in the extract as obtained in the extraction experiments as described hereinabove.

TABLE 3

| G/L (wt/wt) | 6.00 | 7.00 | 8.00 | 9.00 | 10.00 |
|---|---|---|---|---|---|
| EtCHO | 46.20 | 53.90 | 61.55 | 69.04 | 76.07 |
| n-BtOH | 99.84 | 99.90 | 99.93 | 99.95 | 99.96 |
| n-PrOH | 94.32 | 97.39 | 98.67 | 99.24 | 99.52 |

(d) Water washing step

Ethanol was recovered from the extract obtained in the second extraction step as described in paragraph (c) above by using a column, 3.8 mm in inner diameter and 3 meters in height, having Raschig rings filled therein, as a water washing column for washing with water and extracting. In this case, the extract obtained in the second extraction step at the ratio of the extractant of 8 was fed at the rate of 1,200 grams per hour from the bottom of the water washing column, and washing water was fed from the top of the column so as to provide a predetermined ratio of the washing water to the extractant (W/G). In this case, the pressure within the column was set to 100 kg per $cm^2$ and the temperature within the column as a whole was maintained at 40° C. The extract was withdrawn from the top of the column, and the lipophilic impurities were recovered by treating the extract at reduced pressure and vaporizing the extractant only. On the other hand, the raffinate was withdrawn from the bottom of the water washing column and an aqueous ethanol solution was collected by treating the raffinate at reduced pressure and vaporizing the extractant only. The extract and the raffinate were tested for extraction of each ingredient of the impurities and Table 4 below shows the rates of extraction of each ingredient in the experiments for extraction which were carried out in the same manner as described hereinabove. The washing rate was determined on the basis of the following formula:

$$\text{Washing Rate} = \frac{\text{(Amount of each ingredient obtained from raffinate)}}{\text{(Amount of each ingredient fed from extract)}}$$

TABLE 4

| G/L (wt/wt) | 0.05 | 0.06 | 0.07 | 0.08 | 0.09 |
|---|---|---|---|---|---|
| EtOH | 64.24 | 75.85 | 85.66 | 92.70 | 96.83 |
| Me—CHO | 6.81 | 8.17 | 9.54 | 10.90 | 12.26 |
| i-AmOH | 5.63 | 6.76 | 7.88 | 9.01 | 10.13 |
| n-BtOH | 12.37 | 14.84 | 17.31 | 19.79 | 22.26 |
| n-PrOH | 27.16 | 32.58 | 38.00 | 43.39 | 48.76 |
| Et—Ace | 1.51 | 1.82 | 2.12 | 2.42 | 2.73 |
| MeOH | 98.63 | 99.84 | 99.98 | 100.00 | 100.00 |

In removing the lipophilic impurities by extracting the aqueous crude ethanol solution with the carbon dioxide in the liquidized state or carbon dioxide gases in the supercritical state, the process according to the present invention can reduce the ratio of the extractant to a quarter or a half of that to be employed in the conventional processes. Hence, costs of high pressure equipment such as high pressure extracting columns, compressors for carbon dioxide gases, and so on, can be reduced to approximately one third of costs required for the conventional processes. Further, power required for the circulation of carbon dioxide gases can be reduced to lower than approximately one third than the conventional processes.

In addition, in instances where a roughly distilled ethanol solution, having the concentration of ethanol of 80% to 90% by weight, is employed as a raw material, the raffinate having the concentration of ethanol of from 30% to 40% by weight can be obtained in the first extraction step, so that the load to be imposed upon the distilling column can be reduced upon the distillation of the raffinate. When the distilling column of such a type as having a side reboiler is employed and a steam withdrawn from the top of the distilling column is concentrated and applied as a heat source for the reboiler or side reboiler in treating the raffinate, energy and utility costs required for the distilling column can be reduced to a great extent.

We claim:

1. A process for the purification of an aqueous crude ethanol solution, comprising: (a) a first extraction step wherein said aqueous crude ethanol solution is extracted with an extractant for removing lipophilic impurities, except for $C_3$-$C_4$ alcohols, contained in the aqueous crude ethanol solution by subjecting said aqueous crude ethanol solution to extraction with the extractant in a pressurized state, which comprises carbon dioxide in a liquidized state or carbon dioxide gas in a supercritical state; (b) a concentration-distillation step wherein a raffinate obtained in said first extraction step is fed to a distilling column to thereby obtain a highly concentrated aqueous ethanol solution from a top of the distilling column and withdraw a fraction containing $C_3$-$C_4$ alcohols from the distilling column as a side stream; (c) a second extraction step wherein the side stream is brought into contact with the extract in a pressurized state, obtained in said first extraction step, to thereby extract the $C_3$-$C_4$ alcohols contained in the side stream into the extract; and (d) a water washing step wherein the extract in a pressurized state, obtained in the second extraction step, is brought into countercurrent contact with water in a pressurized state under such a condition that a ratio of the weight of the water to the weight of the extract is set to 0.3 or less to thereby recover the ethanol contained in the extract into an aqueous phase.

2. A process for the purification of an aqueous crude ethanol solution as claimed in claim 1, wherein the raffinate obtained in said second extraction step (c) is circulated to said first extraction step (a).

3. A process for the purification, of an aqueous crude ethanol solution as claimed in claim 1, wherein an aqueous phase obtained in said water washing step (d) is mixed with said side stream obtained in said concentration-distillation step (b).

4. A process for the purification of an aqueous crude ethanol solution as claimed in claim 1, wherein said side stream obtained in said concentration-distillation step (b) is mixed with water.

5. A process for the purification of an aqueous crude ethanol solution as claimed in claim 2, wherein an aqueous phase obtained in said water washing step (d) is mixed with said side stream obtained in said concentration-distillation step (b).

6. A process for the purification of an aqueous crude ethanol solution as claimed in claim 2, wherein said side stream obtained in said concentration-distillation step (b) is mixed 7. A process for the purification of an aqueous crude ethanol solution as claimed in claim 3, wherein said side stream obtained in said concentration-distillation step (b) is mixed with water.

* * * * *

UNITED STATES PATENT AND TRADEMARK OFFICE
CERTIFICATE OF CORRECTION

PATENT NO. : 5,284,983
DATED : February 8, 1994
INVENTOR(S) : MUTO et al

It is certified that error appears in the above-indentified patent and that said Letters Patent is hereby corrected as shown below:

Col. 5, line 25, before "according" insert --process--.

Col. 10, line 63, after "mixed" insert --with water.--.

Signed and Sealed this

Thirteenth Day of September, 1994

Attest:

Attesting Officer

BRUCE LEHMAN

Commissioner of Patents and Trademarks